United States Patent [19]

Kelln et al.

[11] Patent Number: 4,764,342
[45] Date of Patent: * Aug. 16, 1988

[54] REAGENT HANDLING

[75] Inventors: Norman G. Kelln; Thomas O. Tiffany, both of Spokane, Wash.

[73] Assignee: Fisher Scientific Company, Pittsburgh, Pa.

[*] Notice: The portion of the term of this patent subsequent to Aug. 2, 2005 has been disclaimed.

[21] Appl. No.: 706,074

[22] Filed: Feb. 27, 1985

[51] Int. Cl.[4] ............................................. G01N 35/02
[52] U.S. Cl. ........................................ 422/72; 141/53;
141/130; 422/63; 422/65; 422/100; 422/102;
436/45; 436/180; 356/246; 356/428
[58] Field of Search .................... 422/63, 64, 65, 72,
422/100, 102; 436/45, 47, 166, 180; 141/130, 5,
325, 326; 356/246, 428; 206/438, 508, 509;
222/585, 588; 220/DIG. 13, 368

[56] References Cited

U.S. PATENT DOCUMENTS

| 643,798 | 2/1900 | Kerstetter | 222/584 |
|---|---|---|---|
| 3,676,076 | 9/1970 | Grady | 422/102 |
| 3,713,985 | 1/1973 | Astle | 422/102 |
| 3,924,471 | 12/1975 | Singer | 141/130 |
| 4,239,853 | 12/1980 | Bradley | 422/72 |
| 4,298,570 | 11/1981 | Lillig et al. | 422/64 |
| 4,391,780 | 7/1983 | Boris | 422/102 |
| 4,456,581 | 6/1984 | Edelmann et al. | 422/100 |
| 4,524,883 | 6/1985 | Herring | 206/509 |

Primary Examiner—Michael S. Marcus

[57] ABSTRACT

A sealed reagent container structure that contains reagent material, has a body portion with length and width dimensions each greater than its height dimension and port defining neck structure, upstanding from the upper wall of the body portion and asymmetrically located so that it is close to one endwall of the body portion. Coupling structure on the bottom wall of the body portion is provided for interengagement with a transport mechanism so that a series of reagent containers may be disposed on the transport mechanism for movement past a reagent station where the reagent material is transferred from the reagent container to the analysis cuvettes for mixing with sample material and analysis.

10 Claims, 3 Drawing Sheets

REAGENT HANDLING

This invention relates to analysis systems, and more particularly to systems for handling reagents for use in analysis systems and to reagent containers for use in such systems.

In a clinical analysis system, raw or dilute sample is frequently mixed with one or more reagents and the resulting reaction is monitored to measure a particular constituent of the sample to be analyzed. For example, in a clinical chemistry analysis system, minute quantities of a serum sample are mixed with various quantities of different reagents to provide chemical reactions that enable measurements of particular constituents of the serum sample.

Clinical analyzers of the centrifugal type are useful in performing a variety of analyses, including kinetic and endpoint analyses, by such techniques as absorption, light scattering and/or fluorescence. In general, such analyzers utilize a multicuvette rotor assembly which has a centrifugal array of spaced elongated radially extending cuvettes, each of which has an inner chamber for initially holding a first reactant which is frequently a sample of blood or other biological fluid, and an outer chamber for initally holding one or more different reactants. The two chambers are separated by divider structure, and the reactants are transferred by centrifugal force to an analysis region at the outer end of the cuvette for mixing and reaction and subsequent analysis. Small quantities of sample (2–20 microliters) typically are loaded into the inner chambers and reactants in quantities of up to about 200 microliters are loaded into the outer chambers. In a typical analysis sequence, the rotor assembly is first spun at 100 rpm, then accelerated to about 4000 rpm for about one second for transferring the reactants from the inner chamber, then braked for mixing the sample and reactants, and then brought up to an analysis speed (typically 500–1000 rpm) for analysis.

Such analyzers are commonly used for the analysis of biological fluids such as blood, blood plasma or serum components, and perform absorbance mode analyses for glucose, cholesterol, creatinine, total protein, calcium, phosphorous, enzymes, and the like; and fluorescence or light scattering mode analyses for glucose, bile acids, phenytoin, pheophylline, gentamycin and the like. To obtain the variety of analyses, a number of different reagents must be available as one or more different reagents are used for each different analysis. A number of different techniques have been used for handling reagents, including storage in the analysis cuvettes, as in the system shown in Rosse U.S. Pat. No. 3,718,439, or dispensing from bulk storage, as in the system shown in Mody U.S. Pat. No. 4,323,537. Such systems have various limitations and complexities.

In accordance with one aspect of the invention, there is provided sealed reagent container structure that contains reagent material, for example as a liquid in ready-to-use form or as a dry powder for reconstitution prior to use. The container has a body portion with length and width dimensions each greater than its height dimension and port defining neck structure upstanding from the upper wall of the body portion and asymmetrically located so that it is close to one endwall of the body portion. Coupling structure on the bottom wall of the body portion is provided for interengagement with a transport mechanism so that a series of reagent containers may be disposed on the transport mechanism for movement past a reagent station where the reagent material is transferred from the reagent container to the analysis cuvettes for mixing with sample material and analysis.

In accordance with another aspect of the invention, there is provided a reagent handling system for use with a clinical analysis system. Transfer structure that includes two fixedly mounted, spaced apart liquid handling probes is movable between a cuvette loading station and sample and reagent supply stations. Sample container and reagent container support mechanisms position sample and reagent containers adjacent at the loading station, with separate drives for independent positioning of different samples and reagents at the sample and reagent stations respectively. The transfer structure includes a drive which concurrently inserts the tips of the two liquid handling probes into containers at the sample and reagent stations and concurrently withdraws sample and reagent material from those containers for transfer to an analysis cuvette at the cuvette loading station. The reagent container support mechanism includes a support surface with container coupling structure. Each reagent container has a body portion with length and width dimensions each greater than the height dimension of the container. Upstanding from the top wall of the container is neck structure that is asymmetrically located in the top wall adjacent the reagent container sidewall adapted to be juxtaposed with a sample container, and that defines a port that is sealed with a probe puncturable membrane that interengages corresponding coupling structure in the bottom wall of the container for secure positioning of the containers on the support mechanism.

In preferred embodiments, the reagent container has a capacity for at least one hundred analyses and is of the single use (disposable) type and a particular embodiment is formed of stretched oriented (blow molded) polymeric material that provides a dedicated reagent storage container from which reagent is withdrawn by the transfer structure without manual pipetting or the use of intermediate containers. A series of protrusions that provide indications of volumetric content of the container are integral with the body. The container coupling structure includes a projection that depends from the bottom wall and carries a machine readable code that is correlated with contents of the container. Air chamber structure is formed in the upper portion of the container above the junction between the body and neck portions, the volume of the air chamber being at least five percent of the total volume of the sealed reagent container. That air chamber structure provides an air reservoir which prevents overfilling of the container, provides a control on the amount of reagent material and provides a mixing region for adequate reagent reconstitution. The container is used both for long term storage of and dispensing of the reagent material and is reliably and releasably coupled to support apparatus for use in automated clinical analysis systems.

In a particular embodiment, the body portion of the container has generally vertical sidewall portions disposed in converging relation to a nose portion that is frictionally secured beneath a flange of the reagent container support mechanism. A group of these reagent containers may be compactly arranged in a circumferential array on a support turntable for indexing relative to the reagent loading station and to a sample container transport mechanism that holds a series of sample containers in a ring coaxial with the reagent container turntable. The reagent container contains a through channel spaced from but adjacent to the port defining neck portion that is sealed to and extends between the top and bottom walls of the body portion, and a sump portion in the bottom wall that is aligned with the neck defining portion for maximizing transfer efficiency of reagent from the container by the transfer structure.

In that particular embodiment, the reagent handling system is used with centrifugal analyzer rotors which have a plurality of analysis cuvettes arranged in annular array, each analysis cuvette having two compartments with loading ports spaced corresponding to the spacing of the two probes of the transfer structure. Indexing mechanism at the cuvette loading station rotates the analyzer rotor to sequentially position cuvettes at the cuvette loading station for loading sample and reagent material from their respective containers under instructions from the system controller.

The system provides improved reagent containers and reagent handling arrangements which permit convenient storage and versatile use of reagents in an automated analysis system so that a number of different tests (profile) can be run utilizing a single analysis rotor and several different reagents on a common sample, as well as other types of analysis procedures such as the batch procedure in which the same analysis is run on several different samples using a single analyzer rotor, for example. The reagent handling containers are easy to load and unload from the transport mechanism and are compatible with the automated reagent handling and analysis systems operable under system control, thus avoiding potential errors and the manual handling aspects of reagents and analysis rotors of prior art analysis systems.

Other features and advantages of the invention will be seen as the following description of a particular embodiment progresses, in conjunction with the drawings, in which:

DESCRIPTION OF PARTICULAR EMBODIMENT

The reagent container 10 shown in FIGS. 1-4 has a body portion 12 of twenty milliliter capacity and is blow molded of high density polyethylene with walls of stretched oriented polymeric material of about one millimeter thickness and corners of about three millimeters radius. Body 12 has a length of about nine centimeters between nose portion 14 and end wall 16, a width of about three centimeters at end wall 16, and a height of about 1.7 centimeters between forward top wall portion 18 and planar bottom wall 20. The rear top wall portion 22 is about three millimeters below the forward wall portion 18 with inclined transition 24 between planar generally vertical sidewalls 26 of container 10 diverge at an angle of about eighteen degrees from nose 14. A series of volume indicating projections 36-1 through 36-5 extend along each junction between side wall 26 and top wall 18 and projecting upwardly from top rear wall portion 22 is cylindrical neck structure 28 that has annular recess 34 and defines circular port 30 that is sealed with probe puncturable membrane 32 of Aclar (chlorotrifluoroethylene) or other suitable material. Cooperating closure cap 40 molded of Kraton has cylindrical wall 42, and top wall 44 with central probe puncturable web section 46 that is about three millimeters in diameter and 0.3 millimeter in thickness and arcuate sections 48 of similar thickness.

Figure 1:
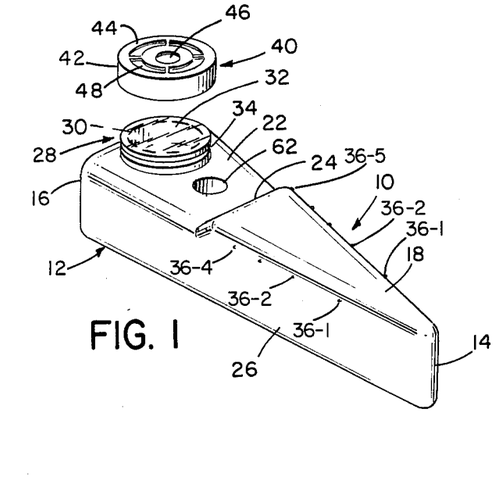
FIG. 1 is a perspective view of a reagent container in accordance with the invention.
Figure 2:
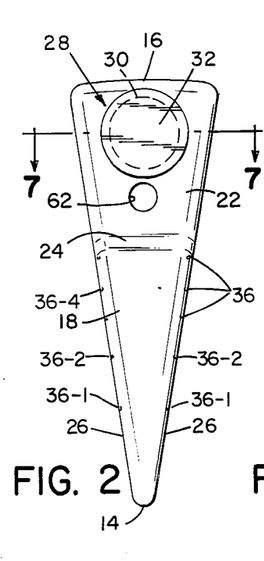
FIG. 2 is a top plan view of the reagent container shown in FIG. 1.
Figure 3:
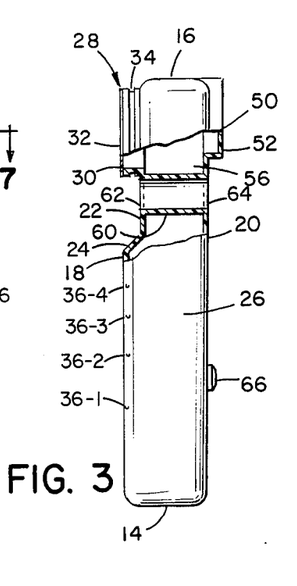
FIG. 3 is a side view (with portions broken away) of the reagent container.
Figure 4:
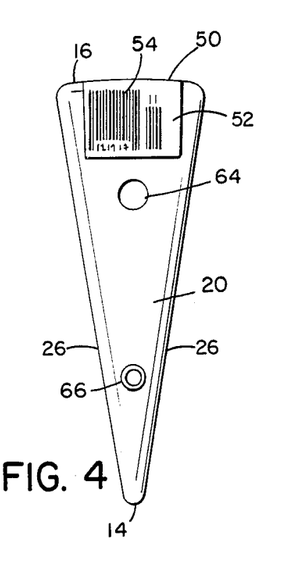
FIG. 4 is a bottom view of the reagent container.

Further details of container 10 may be seen with reference to FIGS. 2-4. Aligned with cylindrical neck structure 28 is generally rectangular sump providing protruberance 50 that is about one-quarter centimeter deep, about 2.2 centimeters wide and about 1.6 centimeters long. As indicated in FIG. 4, on the bottom surface 52 of sump 50 is machine readable barcode information 54 which identifies the reagent material 56 stored in container 10. Forward of sump 50 is cylindrical sleeve 60 (of about 0.6 centimeter diameter) that is sealed to and extends between port 62 in upper wall 22 and port 64 in lower wall 20. Between port 64 and nose 14 is cylindrical container locating projection 66 that has a diameter of about one-half centimeter and a length of about one-quarter centimeter.

The chamber portion provided by the higher level top wall portion 18 and bounded in part by inclined transition wall 24 provides an air pocket region of about two milliliters volume that is effective to limit filling of container 10 and provides a volume for agitation and mixing of the reagent contents, for example when stored dry-form reagent material 56B is reconstituted with a liquid.

Figure 5:
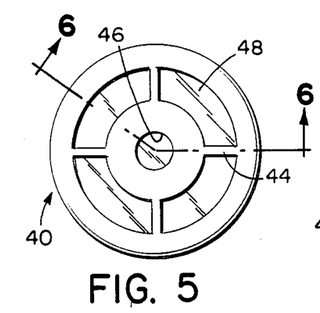
FIG. 5 is a top view of the container cap.
Figure 6:
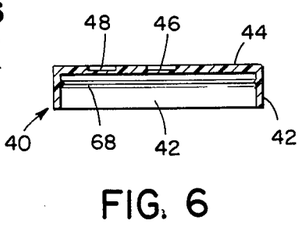
FIG. 6 is a sectional view taken along the line 6—6 of FIG. 5 of the reagent cap.
Figure 7:
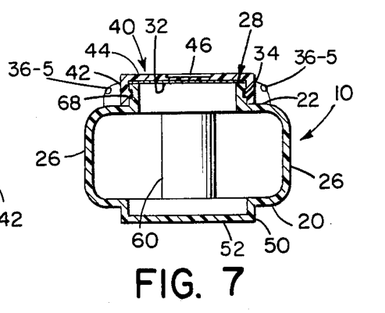
FIG. 7 is a sectional view of the reagent container taken along the line 7—7 of FIG. 2.

Further details of closure cap 40 may be seen with reference to FIGS. 5 and 6. That cap is molded of Kraton and has a diameter of about two centimeters and a height of about 0.4 centimeter. Cylindrical wall 42 has a thickness of about half a millimeter and latch rib 68 (that inwardly projects about 0.2 millimeter) engages recess 34 when cap 40 is on container 10, as shown in the sectional end view of FIG. 7. In that position, cap 40 provides a removable enclosing cover for container 10 that furnishes supplemental reagent protection and reduces evaporation.

Figure 8:
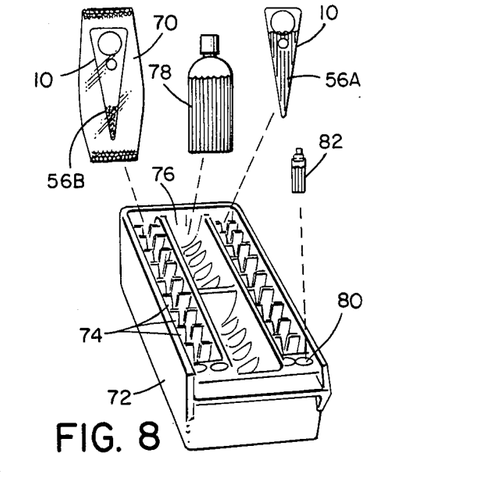
FIG. 8 is a perspective view of reagent container storage structure and associated reagent containers.

A reagent 56 may be stored in container 10 in liquid form (as indicated at 56A in FIG. 8) or in dry powder form (as indicated at 56B) in which case the container may be sealed in envelope 70 to provide supplemental protection for long term storage. Containers 10 may be disposed in storage carton 72 that has compartments defined by partitions 74 for receiving reagent containers 10 as indicated in FIG. 8. Additional receptacles 76 also provided in carton 72 receive bottles of reconstituting liquids 78 and receptacles 80 receive smaller vials 82.

Figure 9:
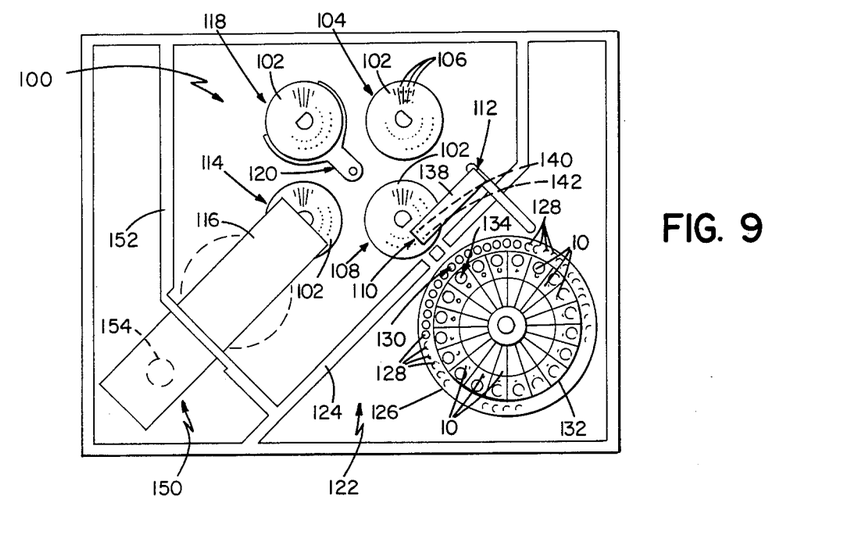
FIG. 9 is a top plan view of a centrifugal analyzer system that uses the reagent containers of the type shown in FIG. 1.

Containers 10 are adapted for use with the centrifugal analyzer shown in diagrammatic view in FIG. 9. That analyzer includes an analysis compartment 100 in which a stack of analysis rotors 102 of the type shown in co-pending application Ser. No. 615,401 filed May 31, 1984 and entitled CUVETTE ROTORS FOR CENTRIFUGAL ANALYZER, the disclosure of which is incorporated herein by reference, are stored at supply station 104. Each rotor 102 has thirty-nine analysis cuvettes 106. Also disposed in analysis compartment 100 is loading table 108 which includes a drive mechanism for indexing a rotor 102 to move its cuvettes 106 past loading position 110 where the chambers of the cuvette are loaded with sample and reagent materials by transfer mechanism 112; analysis station 114 which includes a drive mechanism for spinning the rotor 102 rapidly to transfer reactants from separate cuvette chambers for mixing and then analysis at a speed of about 600 rpm for analysis; optics module 116; and used rotor station 118 where rotors may be temporarily stored after analysis for reuse (if not all cuvettes have been used for analysis) or stacked for discard. Transport mechanism 120 includes arms for grasping a rotor 102 for transport from supply station 104 to loading table 108 where the several cuvettes of the rotor are loaded with sample and reagent materials, then to analysis station 114 where the loaded rotor is driven in rotation for reagent-sample mixing and analysis, and then to used rotor station 118 after the contents of the rotor cuvettes have been analyzed. Further details of apparatus in analysis compartment 100 may be seen with reference to co-pending application Ser. No. 706,073 filed concurrently herewith entitled CUVETTE HANDLING, the disclosure of which is incorporated herein by reference.

The system also includes storage compartment 122 which is separated from analysis compartment 100 by thermal isolation wall 124. Disposed within compartment 122 is transport ring 126 that carries sample cups 128 disposed in circular array for movement past sample station 130; and transport table 132 that has a capacity for twenty reagent containers 10 arranged in circular array for movement of those reagent containers past reagent station 134. A transfer mechanism 112 includes a pipette arm 138 which carries two pipette tubes 140, 142 at its forward end and a drive mechanism for moving arm 138 between loading position 110 in analysis compartment 100 where the tips of the pipettes 140, 142 are aligned with ports in a cuvette 106 of an analysis rotor 102, through an aperture in isolation wall 124 to a position in storage compartment 122 where one pipette is aligned with a sample cup 128 at sample station 130 and a second pipette is aligned with port 30 of a reagent container 10 at reagent station 134 (or a dilution position in which the tips of the pipettes 140, 142 are aligned with ports 30 and 62 of the container 10 at station 134). Further details of the transfer mechanism 112 may be had with reference to co-pending application Ser. No. 599,509 filed Apr. 12, 1984 entitled LIQUID HANDLING, the disclosure of which is incorporated herein by reference. Housed in a third compartment 150 that is separated from analysis compartment 100 by thermal isolation wall 152 is radiation source 154 which operates in conjunction with optics module 116 for photometric analysis of samples in the rotor 102 at analysis station 114.

Figure 10:
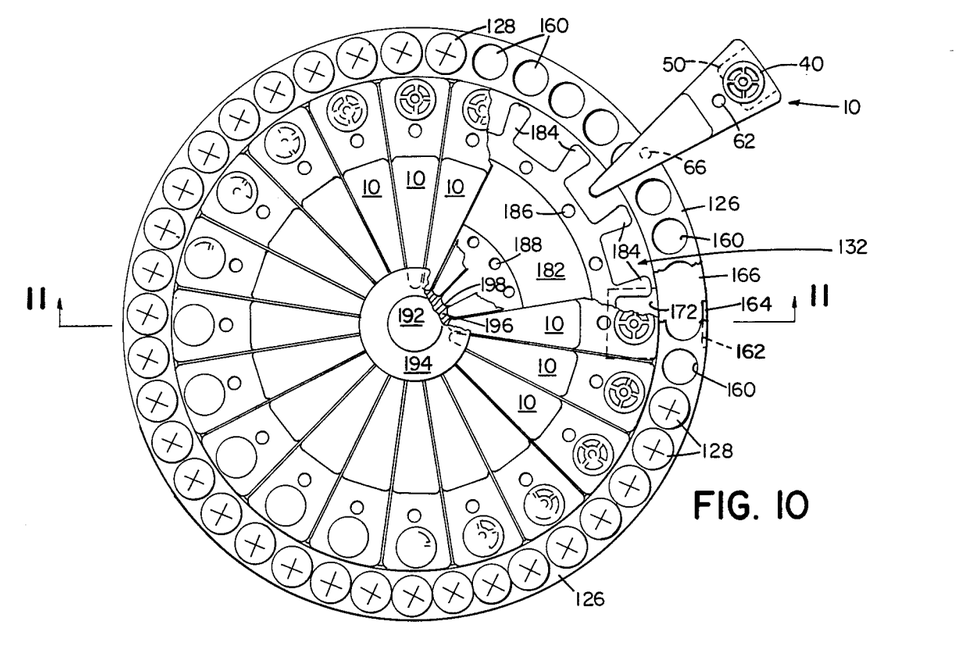
FIG. 10 is a top plan view showing details of reagent and sample container handling mechanisms employed in the analyzer shown in FIG. 9.
Figure 11:
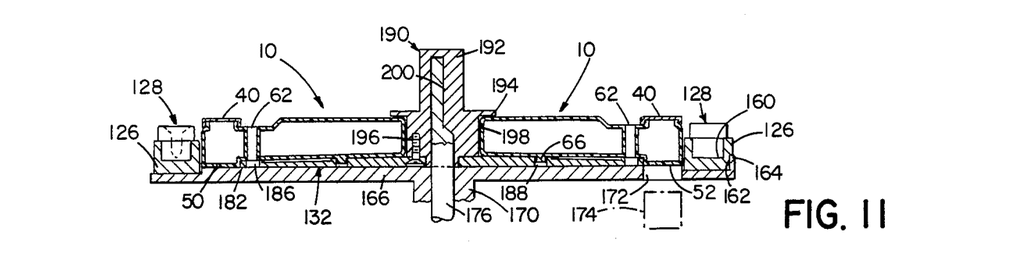
FIG. 11 is a sectional view taken along the line 11—11 of FIG. 10.
Figure 12:
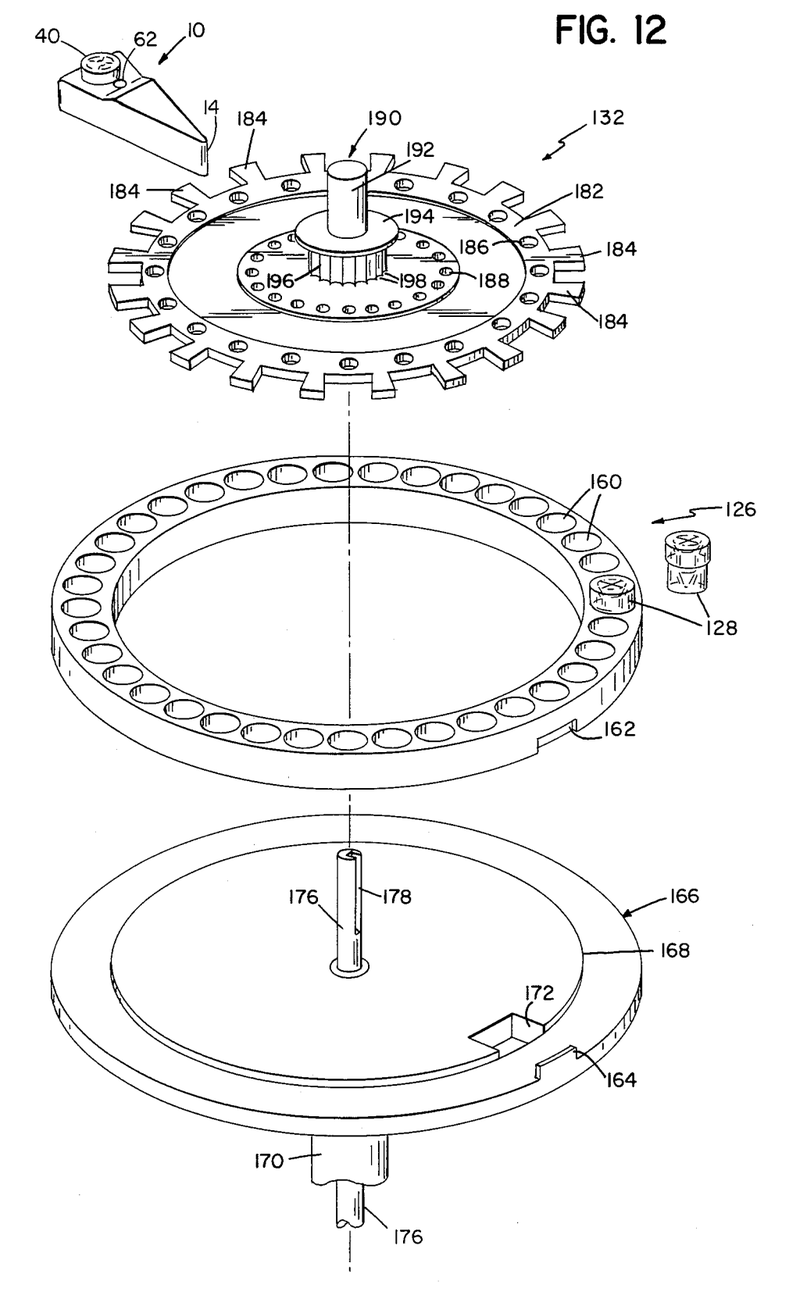
FIG. 12 is an exploded perspective view of components of the reagent and sample container handling mechanisms.

Further aspects of the sample and reagent transport mechanisms 126 and 132 may be seen with reference to FIGS. 10-12. Sample ring 126 has a series of forty-four sockets 160 which receive sample cups 128, each of which has a capacity of about one-quarter milliliter. Transport ring 126 has a drive socket 162 which engages drive production 164 on drive table 166 (FIGS. 11 and 12). Table 166 also includes a cylindrical aligning ridge 168 and a depending hub 170 that is coupled to a stepper motor (not shown) for indexing sample ring 126 past sample station 130, the drive for ring 126 requiring forty steps to index ring 126 one sample position. Aperture 172 in drive table 166 is alignable with optical reader 174 that is mounted beneath table 166 as indicated in FIG. 11.

Extending through hub 170 of sample ring drive table 166 is drive shaft 176 that has a drive coupling 178 at its upper end. Received on drive shaft 176 is reagent container transport turntable 132. Turntable 132 includes radially extending plate 182 that has a diameter of about twenty-one centimeters and a thickness of about one-quarter centimeter. Radially projecting fingers 184 at the periphery of plate 182 define a series of twenty recesses, each of which has a width of about 2.2 centimeters and a radial depth of about 1.2 centimeters. Radially inward of and aligned with each recess is an 0.6 centimeter diameter aperture 186 and a one-half centimeter diameter aperture 188. Attached to the center of plate 182 is hub 190 that has an upper handle portion 192 of about two centimeters in diameter, intermediate flange 194 of about five centimeters diameter and base portion 196 of about four centimeters diameter which has a series of twenty cylindrical alignment recesses 198 formed about its periphery. Formed in the socket of hub 190 is a drive key 200 that engages drive coupling 178 when turntable 132 is seated on table 166.

Each reagent container 10 is loaded onto table 132 with its nose 14 frictionally secured under flange 194 and seated in an alignment recess 198, aligning projection 66 seated in inner alignment aperture 188 and rectangular sump 50 seated in the recess defined between adjacent fingers 184 so that the reagent containers 10 are securely positioned on table 132. In this position, each through passage sleeve 60 is aligned with an intermediate aperture 186. The table 132 loaded with reagent containers 10 is then inserted onto upstanding shaft 176 in driving engagement therewith as indicated in FIG. 11. After table 180 is so positioned, sample support table 166 is indexed to position aperture 172 in alignment with optical reader 174, and then table 132 is indexed by a stepper motor via shaft 176 (forty steps per reagent position) to read the barcode information 54 on the reagent containers 10 and store that reagent identification information in the memory of the analyzer control system. The position of each of the twenty reagent containers 10 is established with reference to slot 178 of drive shaft 176. Similarly, the angular position of each of the sample containers 128 is established relative to drive hub 170 by the interengaged notch 162 and key 164.

In system operation to transfer sample and reagent from containers 10 and 126 to a cuvette 106 of a rotor 102 at loading station 108, transfer arm 138 moves the pipettes 140, 142 into alignment with the selected reagent and sample containers that have been positioned at the sample and reagent loading stations by their respective drives. When an analysis is to employ two reagents, transport arm 136 is moved so that the tip of pipette 140 is aligned with the reagent container port 30 while tip of pipette 142 is aligned with the through channel port 62; the transport arm is lowered to insert the tip of pipette 140 through membrane 32 or cap web 46 into the reagent in the container 10 at the reagent station while pipette 142 passes into channel 60, and the metering syringe draws a specified volume of a reagent into pipette 140. The transfer arm 138 is then lifted and moved to position pipette 140 at the sample station 130 while the reagent table 132 is indexed to position a second container 10 at reagent position 134; the two pipettes are lowered concurrently into a sample cup 128 and the different reagent container 10 and the volumes of sample and second reagent specified by the system controller are drawn up into the pipettes. The transfer arm 138 is then lifted and moved laterally to the loading station 110, the pipettes lowered through the ports of the cuvette 106 at that loading station 110 and the pipetted volumes of sample and reagents are dispensed into their respective chambers of that cuvette.

After some or all of the thirty-nine cuvettes 106 of rotor 102 have been loaded (again as determined by the system controller), rotor transport mechanism 120 moves the loaded rotor 102 from loading station 110 to analysis station 114 where the rotor 102 is spun to centrifugally mix the sample and reagents and then to perform analyses on the resulting mixtures. After the analyses have been completed, the rotor is moved from the analysis station 114 to the temporary storage station 118 and the next rotor (previously taken from the supply stack for transfer to loading station 110 for loading in the above described manner) is moved to analysis station 114.

While a particular embodiment of the invention has been shown and described, various modifications will be apparent to those skilled in the art, and therefore it is not intended that the invention be limited to the disclosed embodiment, or to details thereof, and departures may be made therefrom within the spirit and scope of the invention.

What is claimed is:

1. Sealed reagent container formed of stretched oriented polymeric material comprising a body portion that has length and width dimensions each greater than its height dimension, said body portion having generally vertical sidewall portions extending between a top wall and a bottom wall, said sidewall portions being disposed in converging relation and joining at a nose portion and an end wall disposed at an end of said container opposite said nose portion, said end wall extending between said sidewall portions and said top and bottom walls, reagent material contained in said body portion, a port-defining neck portion formed in said top wall of said body portion and upstanding from the top wall of said body portion, said port-defining neck portion being asymmetrically located so that it is close to the endwall of said body portion remote from said nose portion, coupling structure on the bottom wall of said body portion positioned and arranged for interengagement with a transport mechanism so that a series of said reagent containers may be disposed on such a transport mechanism for movement past a reagent station where the reagent material is transferred from the reagent container to analysis cuvettes for mixing with sample material an analysis; structure defining a through channel spaced from but adjacent to said port defining neck portion, said through-channel defining structure being open at it top and at its bottom and being sealed to and extending between the top and bottom walls of said body portion; and means for sealing said port.

2. The container of claim 1 wherein said reagent container coupling structure includes a projection that depends from the bottom wall and said projection carries a machine readable code that is correlated with said reagent material.

3. The container of claim 1 wherein said means for sealing said port comprises a probe puncturable membrane positioned and arranged across said neck portion, and further including removable closure cap structure releasably engaged with said neck portion.

4. The container of claim 1 wherein said top wall includes a portion defining an air chamber structure extending above a junction between said body and neck portions located adjacent said nose portion, the volume of said air chamber being a least five percent of the total volume of the sealed reagent container.

5. The container of claim 1 wherein the quantity of reagent material in said container is sufficient for at least one hundred analyses, the body portion of said container has a sump portion formed in the bottom wall aligned with said neck portion for maximizing transfer efficiency of reagent from said container, and a bottom external surface of said sump portion carries a machine readable code that is correlated with said reagent material.

6. The container of claim 5 wherein said means for sealing said port comprises a probe puncturable membrane, and further including removable closure cap structure releasably engaged with said neck portion.

7. A reagent handling system for use with a clinical analysis system comprising:
a cuvette loading station and sample and reagent supply stations disposed along a straight line path;
transfer structure that includes two spaced apart liquid handling probes fixedly mounted thereon and aligned with said straight line path, means for moving said transfer structure along said straight line path between a first transfer location in said cuvette loading station, a second transfer location in said sample supply station and a third transfer location in said reagent supply station;
a centrifugal analyzer rotor positioned and arranged in said cuvette loading station and having a plurality of analysis cuvettes arranged in annular array therein, each said analysis cuvette having two loading ports spaced a distance corresponding to the spacing of the two probes of said transfer structure, and indexing mechanism at said cuvette loading station positioned and arranged for rotating the analyzer rotor to sequentially position said cuvettes at said first transfer location in the cuvette loading station for loading sample and reagent material from said sample and reagent supply stations, respectively, into said cuvettes under instructions from a system controller;
said sample station including sample container turntable means for selectively positioning a sequence of sample containers in said second transfer location; said reagent station including reagent container turntable means coaxial with said sample container turntable means for selectively positioning a sequence of reagent containers in said third transfer location; means sfor separately driving said sample container turntable means and said reagent container turntable means for independently positioning different sample and reagent containers in said second transfer location and said third transfer location, respectively, said reagent container turntable means including a support surface with container coupling means, and a plurality of reagent containers on said reagent container turntable mechanism, each said reagent container having a body portion with length and width dimensions each greater than the height dimension of the container, the body portion of each said container having generally vertical sidewall portions extending between a top wall and a bottom wall, said sidewall portions being disposed in converging relation and joining at a nose portion, an end wall being disposed at an end of said container opposite said nose portion and extending between said sidewall portions and said top and bottom walls, a port-defining neck portion formed in said top wall of said body portion and upstanding from the top wall of each said reagent container, said port-defining neck portion being asymmetrically located adjacent that reagent container sidewall which is remote from said nose portion and the bottom wall of each said reagent container including a coupling structure that interengages said container coupling means of said support surface of said reagent container turntable means for secure positioning on said reagent container turntable means, the body portion of each said container having structure defining a through-channel spaced from said port-defining neck portion a distance corresponding to the spacing of said probes, said through-channel defining structure being open at its top and at it bottom and being sealed to and extending between the top and bottom walls of said body portion, said plurality of reagent containers being compactly arranged in a circumferential array on said support surface of reagent container turntable means for indexing relative to said third transfer location of said reagent loading station, said sample container turntable means holding a series of sample containers in a ring coaxial with said reagent container turntable means, said transfer structure including a drive means for concurrently inserting tips of said two liquid handling probes into sample and reagent containers located at said second and third transfer locations, respectively, and concurrently withdrawing sample and reagent material therefrom for transfer to an analysis cuvette at said first transfer location in said cuvette loading station.

8. The system of claim 7 wherein said reagent container turntable means includes a series of apertures formed therein and said system further includes a code reader aligned with said apertures, and each said reagent container has a projection that depends from its bottom wall for disposal in a said aperture and carries a machine readable code that is correlated with contents of the container and positioned and arranged to be read by said code reader.

9. The system of claim 8 wherein each said reagent container is formed of stretched oriented polymeric material and the quantity of reagent material in said reagent container is sufficient for at least one hundred analyses.

10. The system of claim 9 wherein the top wall of said reagent container includes a portion defining an air chamber structure extending above the junction between said body and neck portions, a volume of said air chamber being at least five percent of the total volume of the reagent container.

* * * * *

UNITED STATES PATENT AND TRADEMARK OFFICE
CERTIFICATE OF CORRECTION

PATENT NO. : 4,764,342

DATED : August 16, 1988

INVENTOR(S) : Norman G. Kelln, et al.

It is certified that error appears in the above-identified patent and that said Letters Patent is hereby corrected as shown below:

The following references cited in the Information Disclosure Statement were omitted from the patent:

| U.S. Pat. No. | Date | Name |
| --- | --- | --- |
| 3,081,115 | 3/1963 | Winter |
| 3,801,283 | 4/1974 | Shapiro |
| 4,298,571 | 11/1981 | DeFulvio |
| 4,311,667 | 1/1982 | Gocho |
| 4,313,735 | 2/1982 | Yamashita |
| 4,341,736 | 7/1982 | Drbal |
| 4,344,768 | 8/1982 | Parker |
| 4,360,360 | 11/1982 | Chiknas |
| 4,373,812 | 2/1983 | Stein |

Hitachi 705, (1981), Fully Automated Chemistry Analyzer, Boehringer Mannheim Diagnostics.

Col. 1, line 42, "move" should be --mode--.

Col. 7, claim 1, line 66, "it" should be --its--.

Col. 8, claim 4, line 14, after "portion" insert --and--;
line 15, "a" should be --at--.

Col. 8, claim 7, line 63, "sfor" should be --for--.

Col. 9, claim 7, line 31, "it" should be --its--.

UNITED STATES PATENT AND TRADEMARK OFFICE
CERTIFICATE OF CORRECTION

PATENT NO. : 4,764,342

DATED : August 16, 1988

INVENTOR(S) : Norman G. Kelln, et al.

It is certified that error appears in the above-identified patent and that said Letters Patent is hereby corrected as shown below:

Col. 9, claim 7, line 31, "it" should be -- its --.

Signed and Sealed this

Twenty-third Day of May, 1989

Attest:

DONALD J. QUIGG

*Attesting Officer*

*Commissioner of Patents and Trademarks*